(12) United States Patent
Franceus et al.

(10) Patent No.: US 12,090,408 B2
(45) Date of Patent: *Sep. 17, 2024

(54) BACKGROUND PROCESS FOR IMPORTING REAL-WORLD ACTIVITY DATA INTO A LOCATION-BASED GAME

(71) Applicant: Niantic, Inc., San Francisco, CA (US)

(72) Inventors: Paul M. Franceus, San Francisco, CA (US); Daphne Alesia Larose, El Cerrito, CA (US); Ethan Jacob Chan, San Francisco, CA (US); Joshua Y. Tang, San Francisco, CA (US); Sang-Min Park, Sammamish, WA (US); Yuegang Mao, Auburn, WA (US); Rowan Rebholz Meara, Seattle, WA (US); Laura Mae Warner, Bellevue, WA (US); Matthew Kiichi Slemon, Redmond, WA (US); James William Otermat, San Leandro, CA (US)

(73) Assignee: NIANTIC, INC., San Francisco, CA (US)

( * ) Notice: Subject to any disclaimer, the term of this patent is extended or adjusted under 35 U.S.C. 154(b) by 636 days.

This patent is subject to a terminal disclaimer.

(21) Appl. No.: 17/228,285

(22) Filed: Apr. 12, 2021

(65) Prior Publication Data
US 2021/0228988 A1     Jul. 29, 2021

Related U.S. Application Data

(63) Continuation-in-part of application No. 16/523,900, filed on Jul. 26, 2019, now Pat. No. 11,007,429.

(51) Int. Cl.
*A63F 13/65*   (2014.01)
*A63F 13/216*  (2014.01)
*A63F 13/35*   (2014.01)

(52) U.S. Cl.
CPC ............ *A63F 13/65* (2014.09); *A63F 13/216* (2014.09); *A63F 13/35* (2014.09)

(58) Field of Classification Search
None
See application file for complete search history.

(56) References Cited

U.S. PATENT DOCUMENTS

| | | | |
|---|---|---|---|
| 7,311,605 B2 | 12/2007 | Moser | |
| 2018/0316702 A1 | 11/2018 | Gaspard | |
| 2018/0361248 A1* | 12/2018 | Nomura | ............... A63F 13/847 |
| 2019/0022530 A1* | 1/2019 | Kornmann | ............. H04W 4/02 |
| 2019/0139321 A1 | 5/2019 | Kocharlakota et al. | |
| 2020/0330874 A1* | 10/2020 | Nomura | .................. A63F 13/65 |

OTHER PUBLICATIONS

United States Office Action, U.S. Appl. No. 16/523,900, filed Aug. 24, 2020, seven pages.

* cited by examiner

*Primary Examiner* — Ronald Laneau
(74) *Attorney, Agent, or Firm* — FENWICK & WEST LLP (57) ABSTRACT

Events in an interactive application (e.g., a location-based parallel reality game) are triggered by a user's real-world activity meeting one or more criteria. A background process executing on the user's client device periodically extracts activity data from an activity monitoring application (e.g., a fitness application) and provides it to a server hosting the interactive application. The server determines whether received activity data triggers an event and, if so, sends a notification of the event to the client device.

19 Claims, 7 Drawing Sheets

BACKGROUND PROCESS FOR IMPORTING REAL-WORLD ACTIVITY DATA INTO A LOCATION-BASED GAME

CROSS REFERENCE TO RELATED APPLICATIONS

This application is a continuation-in-part of co-pending U.S. application Ser. No. 16/523,900.

TECHNICAL FIELD

The present disclosure relates generally to location-based gaming and, in particular, to a background process for importing real-world activity data into such games.

BACKGROUND

Location-based games use the real world as their geography. Parallel reality games are a type of location-based game that use a virtual world that parallels the real-world geography. Players can interact and perform various game objectives in the parallel virtual world by navigating and performing actions in the real world. However, when actions are primarily undertaken with reference to the virtual world, the virtual world can act as a barrier to players experiencing the virtual world as truly parallel to the real world. Rather, players may experience the real and virtual worlds as distinct and relatively unconnected.

SUMMARY

In a location-based, parallel reality game, players navigate a virtual world by travelling through the real world with a location-aware client device such as a smartphone. The game may include game objectives that are tied to the player's physical activity in the real world. For example, the player may need to travel a certain distance in the virtual world (and thus a corresponding distance in the real world) to unlock an in-game reward or bonus.

Many client devices that may be used to play such a game already include activity tracking applications (e.g., fitness applications) that generate activity data. In various embodiments, a player's client device executes a background process that periodically extracts the activity generated by an activity tracking application and sends it to a server that hosts the location-based parallel reality game. The game server updates cumulative activity statistics for the player based on the extracted activity data. If the update to the cumulative activity statistics results in the occurrence of an in-game event, the game server sends a notification to the player's client device for display. Thus, players may be notified of in-game events that are triggered by their real-world activity without opening the game itself. This may increase engagement of players with the location-based parallel reality game.

DETAILED DESCRIPTION

Reference will now be made to several embodiments, examples of which are illustrated in the accompanying figures. Wherever practicable, similar or like reference numbers are used in the figures to indicate similar or like functionality. Where similar elements are identified by a reference number followed by a letter, a reference to the number alone in the description that follows may refer to all such elements, any one such element, or any combination of such elements. Although the embodiments described relate to a parallel reality game, one of skill in the art will recognize that the disclosed techniques may be applied with other interactive applications.

Overview

A parallel reality game occurs in a virtual world in which virtual locations are mapped to real world locations. The virtual world has experiences that relate to real world actions, such experiences incorporating virtual elements, such as virtual objects, virtual items, virtual energy, and other virtual elements, that can be used, collected, or interacted with by players of a parallel reality game having a virtual world that parallels at least a portion of the real world. In particular, the experiences in the virtual world are determined based on data associated with one or more real world actions. For example, the outcome or progression of in-game experiences may be impacted by the real-world activity of players. This improves the link between the parallel virtual world and the real world, further enhancing the illusion that the virtual world is another dimension of the real world that the player can perceive and interact with through the parallel reality game. This in turn may make game play more immersive.

A game server can host a location-based parallel reality game having a player gaming area that includes a virtual game environment with a geography that parallels at least a portion of the real-world geography. Players can navigate a virtual space in the virtual world by navigating a corresponding geographic space in the real world. In particular, players can navigate a range of coordinates defining a virtual space in the virtual world by navigating a range of geographic coordinates in the real world.

In one aspect, the positions of players can be monitored or tracked using, for instance, a positioning system (e.g., a GPS system) associated with a player's mobile client device (e.g., a cell phone, smartphone, gaming device, or other device). As players move about in the real world, player position information can be provided to the game server hosting the parallel reality game over a network. The game server can update player positions in the parallel virtual world to correspond with the player positions in the real world.

The parallel reality game can include one or more virtual elements that players can interact with during the course of the parallel reality game. To interact with virtual elements, a player may have to travel to the corresponding location of the virtual element in the real world and perform any necessary interactions in the parallel reality game. According to aspects of the present disclosure, virtual experiences can be generated in the virtual world based on data associated with real world actions. The data associated with real world actions can be analyzed to determine experiences in the virtual worlds. For instance, a virtual experience may require a player to travel a certain distance in the virtual world, and thus to travel a corresponding distance in the real world. The travel may be limited by one or more conditions (e.g., no faster than a maximum speed, within a certain time range, in certain directions, etc.) with real world travel that does not meet the conditions not contributing to the travel requirement in the virtual world. Similarly, a virtual experience may require a player to maintain a certain level of activity (e.g., sensor data generated by the player's client device indicative of the player exercising) for a certain amount of time.

Tying virtual experiences to real world actions permits a more engaging experience for players by improving the link between the real world and the parallel virtual world. The link between the real and virtual worlds may be further improved by enabling real world actions taken by a player when not playing the parallel reality game to impact the virtual world. Many client devices collect activity data such as estimates of steps taken, wheelchair pushes, minutes spent exercising, and calories burned. In various embodiments, activity data may be gathered and imported into a parallel reality game using a background process. Thus, a player may be credited in-game for real-world activity taken while the game is not running (or is running in the background rather than being actively played). The player may also be notified (e.g., using a push notification) when imported activity data results in an update to an in-game experience (e.g., if a distance travelled goal has been reached making an in-game reward available). Consequently, player engagement with the parallel reality game may be increased.

Other exemplary applications of data associated with real world actions can include two or more players working together in the real world to achieve one or more goals in the virtual world as a virtual experience. As an example, the virtual experiences in the virtual world can include shared virtual experiences in which two or more players collaborate to achieve a mutual objective in the virtual world. For example, a group of players may all receive an in-game reward for meeting a collective distance travelled goal. This may increase social interactions relating to the game and provide a more rewarding player experience.

Exemplary Location-Based Parallel Reality Gaming System

Figure 1:
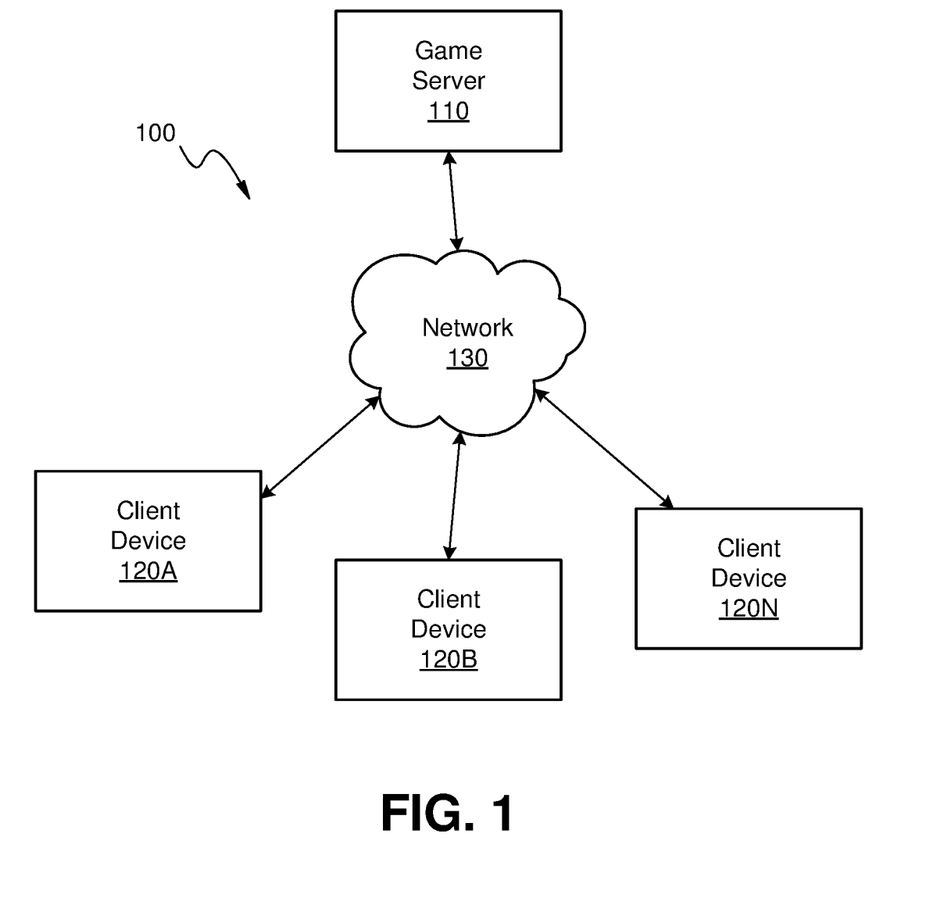
FIG. 1 is a block diagram illustrating a networked computing environment suitable for operating a location-based game, according to one embodiment.

FIG. 1 illustrates an embodiment of distributed location-based gaming system 100. The location-based gaming system 100 provides for the interaction of players in a virtual world having a geography that parallels the real world. In particular, a geographic area in the real world can be linked or mapped directly to a corresponding area in the virtual world. A player can move about in the virtual world by moving to various geographic locations in the real world. The system 100 can track a player's position in the real world and update the player's position in the virtual world based on the player's current position in the real world. For example, a coordinate system in the real world (e.g., longitude and latitude) may be mapped to a coordinate system in the virtual world (e.g., x/y coordinates, virtual longitude and latitude, etc.).

In the embodiment shown in FIG. 1, the distributed location-based gaming system 100 includes a game server 110 and client devices 120 connected via a network 130. Although three client devices 120 are shown, any number of client devices can be connected to the game server 110 via the network 130. In other embodiments, the distributed location-based gaming system 100 includes different or additional elements. Furthermore, the functions may be distributed among the elements in a different manner than described.

The game server 110 hosts a master state of the location-based game and provides game status updates to players' client devices 120 (e.g., based on actions taken by other players in the game, changes in real-world conditions, changes in game state or condition, etc.). The game server 110 receives and processes input from players in the location-based game. Players may be identified by a username or player ID (e.g., a unique number or alphanumeric string) that the players' client devices 120 send to the game server 110 in conjunction with the players' inputs.

For example, the game server 110 may receive a request from a client device 120 for a corresponding player to perform an in-game action. The request may include an identifier of the player and information about the requested action, such as the identity of an object with which the player wishes to interact and the nature of the requested interaction (e.g., pick up, drop, capture, upgrade, etc.). The game server 110 may determine the outcome and return a game update to the client device based on the determined outcome. The game server 110 also receives real-world activity data from players' client devices 110 and determines in-game outcomes based on the real-world activity data. The game server 110 may also notify players (e.g., via a push notification) of certain in-game outcomes resulting from the real-world activity data. Various embodiments of the game server 110 are described in greater detail below, with reference to FIG. 5.

The client devices 120 are computing devices with which players can interact with the game server 100. For instance, a client device 120 can be a smartphone, portable gaming device, tablet, personal digital assistant (PDA), cellular phone, navigation system, handheld GPS system, or other such device. A client device 120 may execute software (e.g., a gaming application or app) to allow a player to interact with the virtual world. A client device 120 may also include hardware, software, or both for generating activity data based on real-world activity of the player, such as a step count or a number of minutes a day spent exercising, etc. A client device 120 may execute a background process that periodically or in response to certain trigger events provides activity data to the game server 110. Various embodiments of client device 120 are described in greater detail below, with reference to FIG. 4.

The network 130 can be any type of communications network, such as a local area network (e.g. intranet), wide area network (e.g. Internet), or some combination thereof. The network can also include a direct connection between a client device 120 and the game server 110. In general, communication between the game server 110 and a client device 120 can be carried via a network interface using any type of wired or wireless connection, using a variety of communication protocols (e.g. TCP/IP, HTTP, S1v1TP, FTP), encodings or formats (e.g. HTML, JSON, XML), or protection schemes (e.g. VPN, secure HTTP, SSL).

Figure 2:
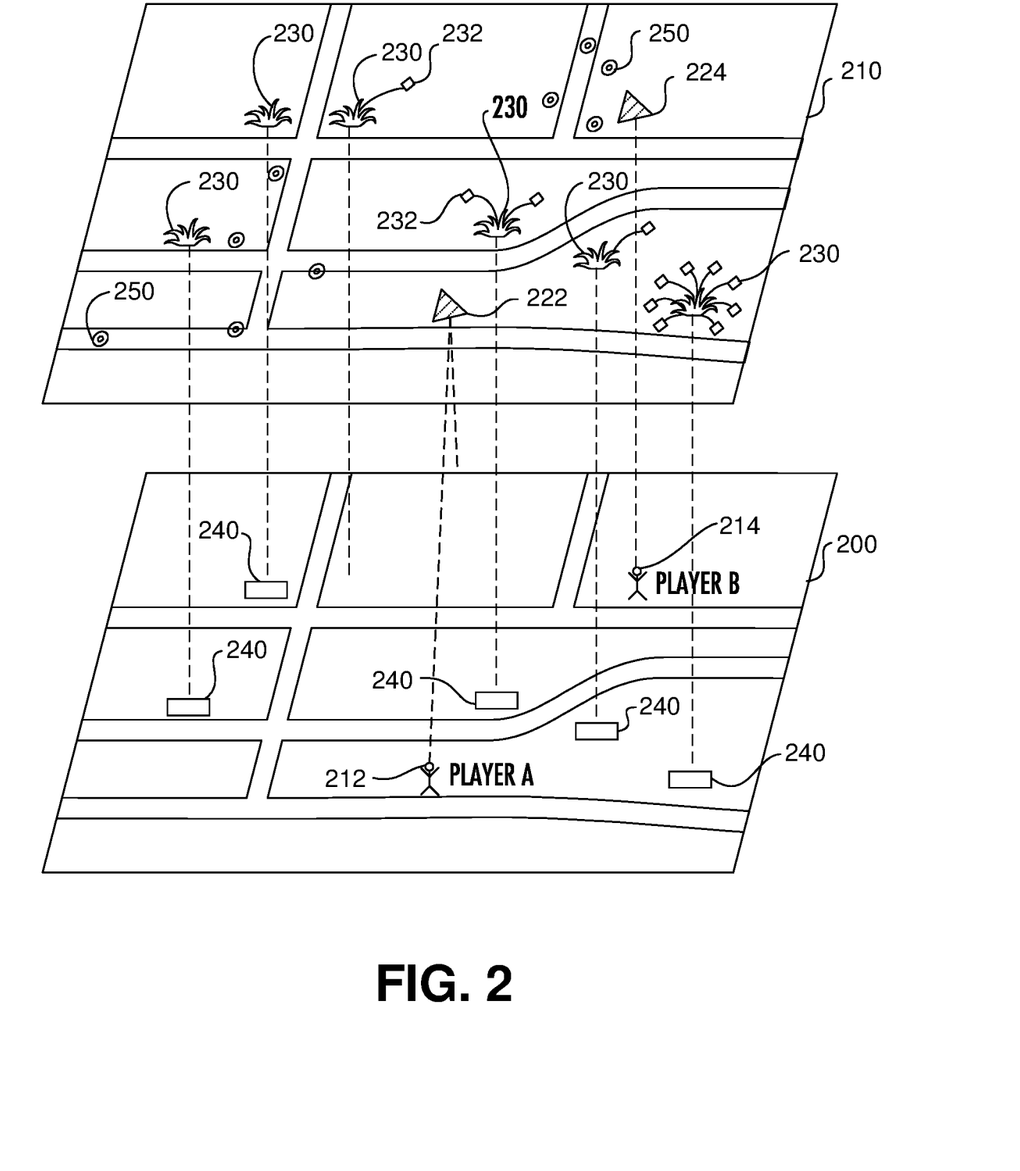
FIG. 2 depicts a representation of a virtual world having a geography that parallels the real world, according to one embodiment.

FIG. 2 is a conceptual diagram illustrating an example parallel-reality virtual world 210 provided by the location-based gaming system 100. The parallel-reality virtual world 210 can act as the game board for players of the location-based game, according to one embodiment. As illustrated, the virtual world 210 includes a geography that parallels the geography of the real world 200. In particular, a range of coordinates defining a geographic area or space in the real world 200 is mapped to a corresponding range of coordinates defining a virtual space in the virtual world 210. The range of coordinates in the real world 200 can be associated with a town, neighborhood, city, campus, locale, a country, continent, the entire globe, or other geographic area. Each geographic coordinate in the range of geographic coordinates in the real world 200 is mapped to a corresponding coordinate in a virtual space in the virtual world 210.

A player's position in the virtual world 210 corresponds to the player's position in the real world 200. For instance, player A, located at position 212 in the real world 200, has a corresponding position 222 in the virtual world 210. Similarly, player B, located at position 214 in the real world 200, has a corresponding position 224 in the virtual world. As the players move about in a range of geographic coordinates in the real world, the players also move about in the range of coordinates defining the virtual space in the virtual world 210. In particular, a positioning system associated with a client device 120 carried by the player (e.g. a GPS system) can be used to track a player's position as the player navigates the range of geographic coordinates in the real world 200. Data associated with the player's position in the real world 200 is used to update the player's position in the corresponding range of coordinates defining the virtual space in the virtual world 210. In this manner, players can navigate a continuous track in the range of coordinates defining the virtual space in the virtual world 210 by simply traveling among the corresponding range of geographic coordinates in the real world 200 without necessarily having to check in or periodically update location information at specific discrete locations in the real world 200.

The location-based game can include game objectives requiring players to travel to or interact with various virtual elements or virtual objects scattered at various virtual locations in the virtual world. A player can travel to these virtual locations by traveling to the corresponding location of the virtual elements or objects in the real world. For instance, a positioning system can continuously track the position of the player such that as the player continuously navigates the real world, the player also continuously navigates the parallel virtual world. The player can then interact with various virtual elements or objects at the specific location to achieve or perform one or more game objectives.

For example, a game objective can include players capturing or otherwise claiming ownership of virtual elements 230 located at various virtual locations in the virtual world 210. These virtual elements 230 can be linked to landmarks, geographic locations, or objects 240 in the real world 200. The real-world landmarks or objects 240 can be works of art, monuments, buildings, businesses, libraries, museums, or other suitable real-world landmarks or objects. To capture these virtual elements 230, a player may travel to the landmark or geographic location 240 linked to the virtual elements 230 in the real world and interact with the virtual elements 230 in the virtual world 210. For example, player A of FIG. 2 may travel to a landmark 240 in the real world 200 in order to interact with or capture a virtual element 230 linked with that particular landmark 240. The interaction with the virtual element 230 can be tied to action in the real world, such as verifying, obtaining, or capturing information about the landmark or object 240 associated with the virtual element 230 (e.g., by taking a photograph).

Game objectives can include that players use one or more virtual items that are collected by the players in the location-based game. For instance, the players may travel the virtual world seeking virtual items (e.g. weapons, food, medical supplies, soldiers, creatures, or other items) that can be useful for completing game objectives. These virtual items can be found or collected by traveling to different locations in the real world or by completing various actions in either the virtual world or the real world. For example, players may interact with virtual elements 230 in the virtual world to obtain virtual items. In the embodiment shown in FIG. 2, a player uses virtual items 232 to capture one or more virtual elements 230. In particular, a player can deploy virtual items 232 at locations in the virtual world 210 proximate the virtual elements 230. Deploying one or more virtual items 232 proximate a virtual element 230 can result in the capture of the virtual element 230 for the particular player or for the player's team or faction.

Game objectives can also include that players meet one or more activity requirements. For instance, players may obtain virtual items that provide in-game rewards (e.g., other virtual items or points) after the player has transported the virtual item a specified distance in the virtual world, which corresponds to travelling a certain distance in the real world. A game objective may limit the travel in the virtual world to being within a specified range of speeds, which corresponds to an average speed in the real world above or below a threshold. The game objectives may be tied to other real-world activity requirements, such as exercise that burns at specified number of calories, time spent sleeping, or time spent engaged in other activities.

In one particular implementation, a player may gather virtual energy as part of the location-based game. As depicted in FIG. 2, virtual energy 250 can be scattered at different locations in the virtual world 210. A player can collect the virtual energy 250 by traveling to the corresponding location of the virtual energy 250 in the actual world 200. The virtual energy 250 can be used to power virtual items or to perform various game objectives in the game. A player that loses all virtual energy 250 can be temporarily disconnected from the game.

According to aspects of the present disclosure, the location-based game can be a massive multi-player location-based game where every participant in the game shares the same virtual world. The players can be divided into separate teams or factions and can work together to achieve one or more game objectives, such as to capture or claim ownership of a virtual element. For convenience, all such groupings of players are referred to as teams. In this manner, the location-based game can intrinsically be a social game that encourages cooperation among players within the game. Players from opposing teams can work against each other during the location-based game. A player can use virtual items to attack or impede progress of players on opposing teams. In some instances, players from different teams may collaborate in certain shared virtual experiences (e.g., boss battles) to achieve a common objective.

The location-based game can have various features to enhance and encourage game play within the location-based game. For instance, players can accumulate a virtual currency or other virtual reward that can be used throughout the game. Players can advance through various levels as the players complete one or more game objectives and gain experience within the game. Players can communicate with one another through one or more communication interfaces provided in the game. Players can also obtain enhanced "powers" or virtual items that can be used to complete game objectives within the game. Those of ordinary skill in the art, using the disclosures provided herein, should understand that various other game features can be included with the location-based game without deviating from the scope of the present disclosure.

Example Game Interface

Figure 3:
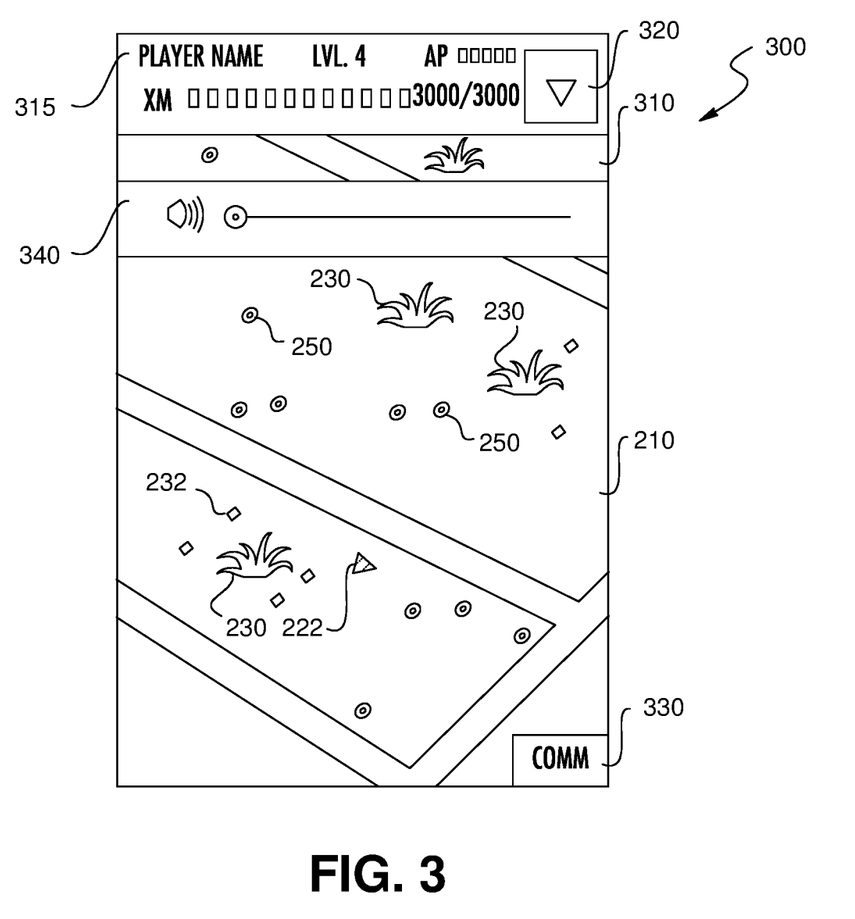
FIG. 3 depicts an exemplary game interface of a location-based game, according to one embodiment.

FIG. 3 depicts one particular embodiment of a game interface 300 that can be presented on a display of a client 120 as part of the interface between a player and the gaming system 100. The game interface 300 includes a display window 310 that can be used to display the virtual world 210 and various other aspects of the game, such as player position 222 and the locations of virtual elements 230, virtual items 232 and virtual energy 250 in the virtual world 210. The user interface 300 can also display other information, such as game data information, game communications, player information, and other information associated with the game. For example, the user interface can display player information 315, such as player name, experience level and other information. The user interface 300 can include a menu 320 for accessing various game settings and other information associated with the game. The user interface 300 can also include a communications interface 330 that enables communications between the game system and the player and between one or more players of the location-based game.

According to aspects of the present disclosure, a player can interact with the location-based game by simply carrying a client device around in the real world. For instance, a player can play the location-based game by simply accessing an application associated with the location based game on a smartphone and moving about in the real world with the smartphone. In this regard, it is not necessary for the player to continuously view a visual representation of the virtual world on a display screen in order to play the location based game. As a result, the user interface 300 can include a plurality of non-visual elements that allow a player to interact with the game. For instance, the game interface can provide audible notifications to the player when the player is approaching a virtual element or object in the game or when an important event happens in the location-based game. A player can control these audible notifications with audio control 340. Different types of audible notifications can be provided to the player depending on the type of virtual element or event. The audible notification can increase or decrease in frequency or volume depending on a player's proximity to a virtual element or object. Other non-visual notifications and signals can be provided to the player, such as a vibratory notification or other suitable notifications or signals.

Those of ordinary skill in the art, using the disclosures provided herein, should understand that numerous game interface configurations and underlying functionalities will be apparent in light of this disclosure. The present disclosure is not intended to be limited to any one particular configuration.

Example Client Device

Figure 4:
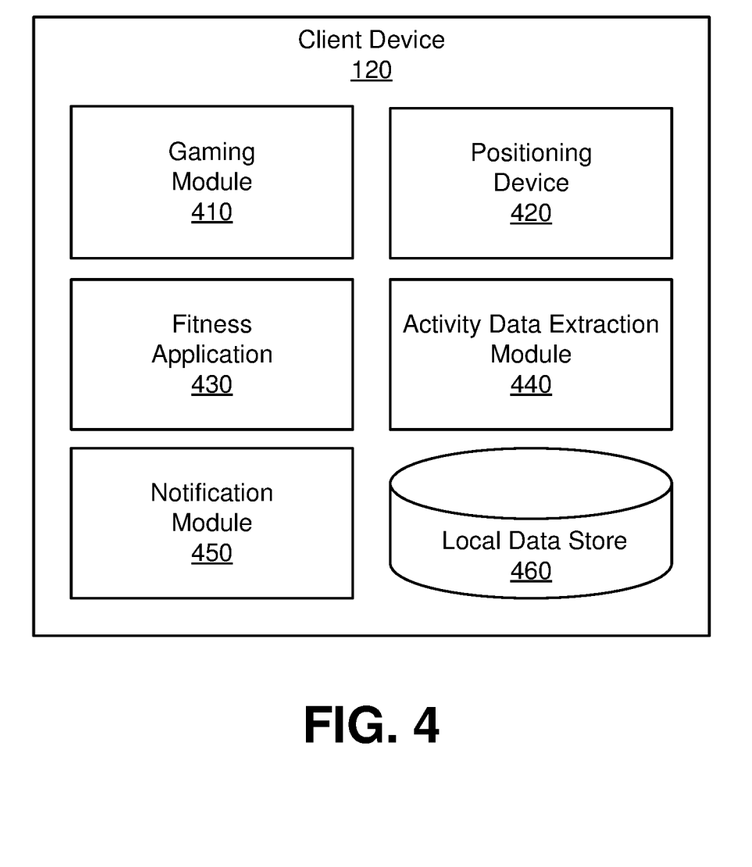
FIG. 4 is block diagram of a client device shown in FIG. 1, according to one embodiment.

FIG. 4 illustrates one embodiment of a client device 120 suitable for use as part of a distributed location-based gaming system 100. In the embodiment shown, the client device 120 includes a gaming module 410, a positioning device 420, a fitness application 430, an activity data extraction module 440, a notification module 450, and a local data store 460. In other embodiments, the client device 120 contains different or additional elements. In addition, the functions may be distributed among the elements in a different manner than described.

The gaming module 410 executed by the client device 120 provides an interface between a player and the location-based game. The gaming module 125 can present a user interface on a display screen associated with the client device 120 (e.g., a built-in screen) that displays the virtual world 210 associated with the game and allows the player to interact with the virtual world to perform various game objectives. The gaming module 410 can also control various other outputs to allow a player to interact with the game without requiring the player to view a display screen. For instance, the gaming module 410 can control various audio, vibratory, or other notifications. The gaming module 410 can access game data received from the game server 110 to provide an accurate representation of the current state of the virtual world 210 to the player. The gaming module 125 can receive and process player input and provide updates to the virtual world 210 to the game server 110 over the network 130.

The positioning device 420 monitors the position of the client device 120. The positioning device 420 can be any device or circuitry for monitoring the position of the client device 120. For example, the positioning device 420 can determine actual or relative position by using a satellite navigation positioning system (e.g., a GPS system, a Galileo positioning system, the Global Navigation satellite system (GLONASS), the BeiDou Satellite Navigation and Positioning system, etc.), an inertial navigation system, a dead reckoning system, by using triangulation or proximity to cellular towers or WiFi hotspots, or other suitable techniques. The position information can be provided on condition of anonymity to protect the privacy of the player.

As the player moves around with the client device 120 in the real world, the positioning device 420 tracks the position of the player and provides player location data to the gaming module 410. The gaming module 410 updates the player's position in the virtual world 210 based on the position of the player in the real world 200. In particular, the location of the player in the virtual world 210 can correspond to the location of the player in the real world 200 (as described previously, with reference to FIG. 2). The gaming module 410 can provide player location data to the game server 110 over the network 130 such that the universal gaming module 510 may keep track of player positions throughout the game.

The fitness application 430 collects activity data for a player associated with the client device 120. The fitness application 430 may be part of the client device's operating system or additional software installed by the player (e.g., an application installed for use with a wearable device such as a smartwatch or fitness tracker). Although the term fitness application 430 is used for convenience, the activity data may be collected by any appropriate activity monitoring application.

The activity data may be derived from the data generated by one or more sensors (e.g., accelerometers, gyroscopes, altimeters, etc.) that may be incorporated into the client device, part of a wearable device, or both. In one embodiment, the activity data includes one or more metrics calculated from the sensor data. The metrics can include totals in a given time period (e.g., in a day), such as steps taken, wheelchair pushes, time spent performing a specified activity (e.g., exercising, running, biking, swimming, etc.), time spent sleeping, and the like. The metrics may also include values of variables over time, such as periodic (e.g., per minute) measures of heart rate, time spent performing a specified activity continuously, time spent sleeping continuously, etc.

The activity data extraction module 440 extracts activity data generated by the fitness application 430 and sends it to the game server 110. In various embodiments, the activity data extraction module 440 executes a background process that periodically (e.g., hourly) checks for updated activity data. The activity data extraction module 440 may filter the activity data based on the source of the activity data. For example, some fitness applications 430 enable a player to manually enter or edit activity data. The activity data extraction module 440 may remove manually inputted data to prevent players from cheating in the parallel reality game by adding activity data to complete game objectives without actually undertaking the required activity. As another example, the activity data extraction module 440 may remove any activity data that is not derived from sensors of an approved device or device type. The activity data extraction module 440 sends the activity data (subject to any filtering applied) to the game server 110 in conjunction with an identifier of the corresponding player (e.g., a player ID or username).

In one embodiment, the fitness application 430 (e.g., HEALTHKIT™ from APPLE®) includes an application programming interface (API) that enables the activity data extraction module 440 to set up a background query. In particular, the activity data extraction module 440 may use the API to configure the fitness application 430 to periodically (e.g., approximately hourly) generate a new data alert if there is new activity data available. In some cases, the new data alert may only be triggered if the client device 120 has been unlocked at some point in the period, which may help preserve battery life by preventing the process from waking up the device if it has not been used during the period. In response to a new data alert, the activity data extraction module 440 checks to determine if the client device 120 has network connectivity and, if so, queries the fitness application 430 for any activity data generated since the previous query and forwards the retrieved activity data to the game server 110.

In another embodiment, rather than receiving data alerts from the fitness application 430, the activity data extraction module 440 periodically (e.g., approximately hourly) determines whether the client device 120 has network connectivity and, if so, the queries the fitness application for any activity data generated since the previous query. This approach may be used where the health application does not provide an API for scheduled activity data updates (e.g., GOOGLE FIT™). The activity data extraction module 440 forwards the retrieved activity data to the game server 110. If the client device 120 is configured with multiple user accounts, the activity data extraction module 440 may prompt the player to select an account for which activity data should be retrieved.

In some embodiments, the activity data extraction module 440 initiates player event sessions as background processes that monitor a location of a client device of a player independently from the regular background processes of the activity data extraction module 440 described above. Player event sessions correspond to certain player events or activities in the real world (e.g., going for a run or a walk) or in the virtual world (e.g., temporal activities, such as growing a virtual flower or training a virtual game character). In particular, a player event session monitors a geographic position of a player using a positioning system of the client device to collect player activity data relevant to the player event corresponding to the player event session. For instance, a player event session may register a notification handler with the positioning system to receive player geographic position updates on a periodic basis (e.g., every twenty seconds) or based on distance moved by the client device (e.g., every fifty meters moved). A player event session may additionally, or alternatively, query the fitness application 430 at a higher, lower, or otherwise different frequency than the regular background processes in order to provide activity data updates to the game server 110 at a corresponding frequency. For example, a user may progress towards achieving a goal in the virtual world much more quickly during periods of heightened athletic activity than during normal activity, such as during a run. As such, the activity data extraction module 440 may initiate a player event session after a user begins heightened athletic activity to query the fitness application 430 more frequently, and similarly may terminate the player event session after the user finishes the heightened athletic activity. As another example, an in-game activity may be associated with a goal that can be achieved relatively quickly (e.g., a goal that can be achieved with a relatively low amount of player activity). In this case, the activity data extraction module 440 may initiate a player event session after the in-game activity begins to monitor the geographic position of the player or query the fitness application 430 more frequently, and may similarly terminate the player event session after the in-game activity ends (e.g., a time limit expires) or the player achieves the goal.

The frequency at which a player event session queries the fitness application 430 may be determined based on various factors, such as based on time (e.g., every five minutes) or based on a query trigger (e.g., every fifty meters moved by the player). For instance, if the query frequency of a player event session is trigger based, the query session may identify when the client device has moved a certain distance (e.g., fifty meters) or moved into a particular geographic area (e.g., a geographic area associated with a virtual event in the virtual world). In other cases, the player event session may use one or more sensors incorporated into the client device to identify an activity data query trigger. If a player event session receives distance information for a player from multiple sources (e.g., a GPS system and an accelerometer), the player event session may select one of the sources to use for identifying query triggers. For instance, the player event session may select the source of distance information that indicates the client device has moved the furthest distance. Additionally, or alternatively, a player event session may receive data alerts or notifications from the fitness application 430 indicating that updated activity data is available, as described above with reference to the fitness application 430 and the activity data extraction module 440.

In some embodiments, the activity data extraction module 440 compares first activity data determined from monitoring the geographic position of the player to second activity data received from the fitness application 430 in order to determine a processed set of activity, e.g., to provide to the game server 110. For example, the activity data extraction module 440 may combine the first and second activity data. Additionally, or alternatively, the activity data extraction nodule may deduplicate information included in both the first and second activity data for the processed set of activity data, such as including only one set information describing a distance moved by the player, etc.

The activity data extraction module 440 may execute multiple data player event sessions with the same or different player position monitoring frequencies or query frequencies in-parallel. For example, the activity data extraction module 440 may execute a first player event session corresponding to activity by a player in the real world and at some time while the first player event session is executing execute a second player event session corresponding to activity in the virtual world. The activity data extraction module 440 may further assign session context information to each player event session. Session context information may include various information describing a player event session, such as a unique session identifier, a session states (e.g., active, inactive, etc.) or other information usable by the client device or the game server 110 for processing data collected by the player event session. In this case, the activity data extraction module 440 may provide the session context information to the game server 110 (e.g., during initiation of the query data session), e.g., to indicate a player event session has been initiated and to facilitate communication between the game server 110 and the player event session. The game server 110 may use the received session context information to identify extracted activity data received from a corresponding player event session. For instance, the game server 110 may use the activity data to determine a relevant player's progression towards a goal corresponding to the player event session.

As an exemplary scenario involving a player event session, a player may initiate an in-game activity that involves the player traveling some distance in the real-world (e.g., one km). In this case, the activity data extraction module 440 may initiate a first player event session corresponding to the in-game activity that identifies a geographic position of a player or queries the fitness application 430 on a periodic basis, such as every six minutes, to determine how far the player has traveled. At some time after initializing the first player event session, the activity data extraction module 440 may identify that the player has begun heightened athletic activity (e.g., running), and initiate a second player event session in-parallel with the first player event session that identifies the geographic position of the player or queries the fitness application 430 at a higher frequency than the first data query session, such as every three minutes. Alternatively, the activity data extraction module 440 may increase the geographic position monitoring or query frequency of the first player event session instead of initializing a second player event session, or terminate the first player event session after initializing the second player event session. After the data extraction module 440 or the game server 110 determines that the player has travelled the distance based on data received from the first or second player event sessions, the data extraction module 440 may terminate the first or second player event sessions.

The notification module 450 presents information relating to the parallel reality game on one or more user interfaces of the client device 110. In one embodiment, the notification module 450 receives push notifications from the game server 110 when the activity data provided by the activity data extraction module 440 indicates the player has completed a game objective (e.g., travelling a specified distance in the virtual world 210, which corresponds to a certain number of steps). The notification module 450 may display a message in a notification bar (e.g., an icon and a short summary of the completed game objective), flash an indicator light (e.g., an LED), cause the client device 120 to vibrate, play a notification sound through a speaker, or otherwise notify the player that the game objective has been completed. In some embodiments, notifications may also be generated indicating the player's progress towards incomplete game objectives to encourage the player to keep working towards completing those objectives. Various ways in which activity data can be imported into the parallel reality game to contribute to completing game objectives are described in greater detail below, with reference to FIG. 5.

The local data store is one or more computer-readable media configured to store data used by the client device 120.

For example, the local data store 460 may store the activity data generated by the fitness application 430, a local copy of the current state of the parallel reality game, or any other appropriate data. Although the local data store 460 is shown as a single entity, the data may be split across multiple media. Furthermore, data may be stored elsewhere (e.g., in a distributed database) and accessed remotely via the network 130.

Example Game Server

Figure 5:
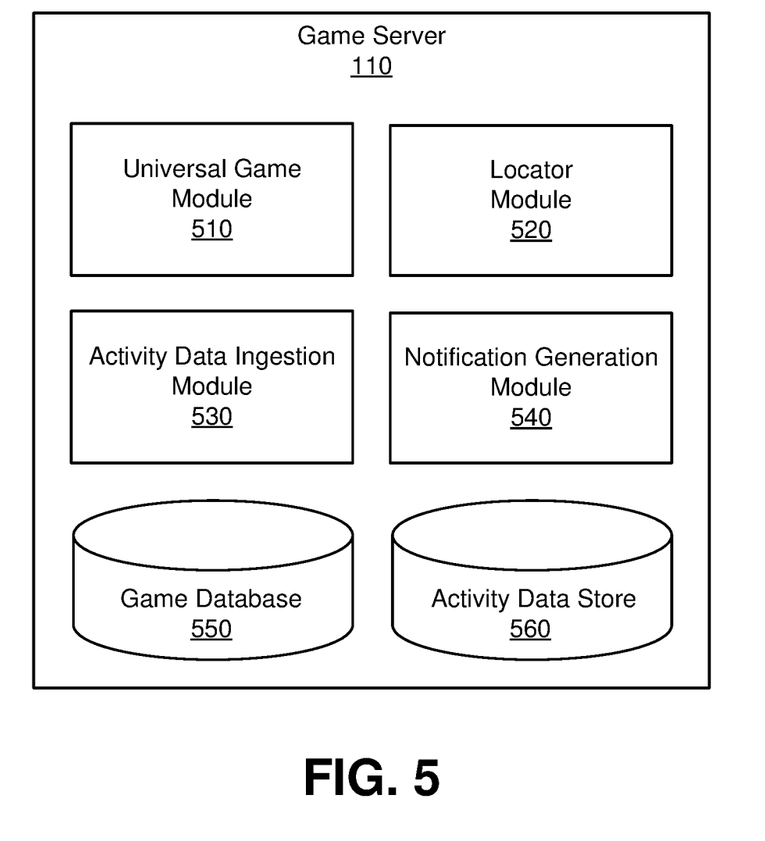
FIG. 5 is a block diagram of the game server shown in FIG. 1, according to one embodiment.

FIG. 5 illustrates one embodiment of the game server 110 suitable for hosting a location-based parallel-reality game. In the embodiment shown, the game server 110 includes a universal game module 510, a locator module 520, an activity data ingestion module 530, a notification generation module 540, a game database 550, and an activity data store 560. In other embodiments, the game server 110 contains different or additional elements. In addition, the functions may be distributed among the elements in a different manner than described.

The game server 110 can be configured to receive requests for game data from one or more clients 120 (for instance, via remote procedure calls (RPCs)) and to respond to those requests via the network 130. For instance, the game server 110 can encode game data in one or more data files and provide the data files to the client 120. In addition, the game server 110 can be configured to receive game data (e.g. player positions, player actions, player input, etc.) from one or more clients 120 via the network 130. For instance, the client device 120 can be configured to periodically send player input, player location, and other updates to the game server 110, which the game server 110 uses to update game data in the game database 550 to reflect changed conditions for the game.

The universal game module 510 hosts the location-based game for players and acts as the authoritative source for the current status of the location-based game. The universal game module 510 receives game data from client devices 120 (e.g., player input, player position, player actions, player status, landmark information, etc.) and incorporates the game data received into the overall location-based game for all players of the location-based game. The universal game module 510 can also manage the delivery of game data to the clients 120 over the network 130.

The universal game module 510 may issue tokens authorizing processes executing on the client devices 120 to access functionality provided by the game server 110. The tokens may be valid for a specified length of time after generation (e.g., one hour, one day, seven days, thirty days, etc.). In one embodiment, when a player logs into the location-based game, the universal game module 510 generates a token for the background process used to extract activity data from the fitness application 430 and sends it to the player's client device 120. The background process token may be valid for an extended period of time (e.g., thirty days) to enable the background process to continue providing activity data, even if the player is not playing the game. Each time the player launches the game, the universal game module 510 may reinitialize the background process token or issue a new token to restart the time period.

The locator module 520 can be a part of or separate from the universal game module 510. The locator module 520 is configured to access data associated with real world actions, analyze the data, and determine virtual experiences in the virtual world based on the data associated with real world actions. For instance, the locator module 520 can modify game data stored in the game database 550 to locate virtual experiences in the virtual world based on the data associated with real world actions. As an example, a sponsored virtual element may be at a virtual location that corresponds to the real-world location of a sponsor's store, restaurant, outlet, etc. If a player makes a purchase, enters a code made available at the real-world location, or takes another action at the real-world location action meeting specified criteria, a special virtual experience may be made available to the player in the parallel reality game.

The activity data ingestion module 530 receives activity data from the client devices (e.g., as extracted by the activity data extraction module 440 of a client device 120) and imports it into the parallel reality game. This may enable players to be credited for their real-world activity when not actively playing the game as well as their real-world activity while playing the game. In one embodiment, the client device 120 initiates a communication session with the game server 110 that identifies a player (e.g., with a player ID or token) and sends activity data. The activity data may indicate a number of steps taken, a number of wheelchair pushes, a real-world distance travelled, an amount of time spent exercising, an amount of time engaged in a specific activity, or any other suitable metric of real-world activity, as well as combinations of the preceding metrics.

The activity data ingestion module 530 may convert some or all of the metrics included in the activity data into virtual-world equivalents, such as converting a number of steps taken or wheelchair pushes into a virtual distance travelled in the virtual world. The activity data ingestion module 530 also updates cumulative activity statistics for the player based on the received activity data (converted, as appropriate). For example, the activity data store 560 may include a total distance travelled by a player as well as the distance travelled in one or more time periods, such as the current day or week, or since a certain item was picked up or activated, etc.

The cumulative activity statistics may be derived from multiple sources of activity data. In one embodiment, the cumulative activity statistics include a distance travelled that is determined from activity data extracted from the fitness application and a distance determined by the gaming module 410 or universal game module 510 while the user is playing a location-based game. The distance travelled may include distances determined by other processes or applications as well. To prevent giving double credit for activity, the activity data ingestion module 530 may identify contributions to the distance travelled determined from different sources that overlap and compensate for the overlap (e.g., by subtracting doubled-counted distance from the total).

The notification generation module 540 sends notifications to players' client devices 120 based on the cumulative activity statistics. In one embodiment, the notification generation module 540 generates a notification when the cumulative activity statistics indicate the player has completed a game objective. The notification is sent to the client device 120 of the player for presentation, as described previously with reference to FIG. 4. For example, a game objective may require a player to obtain or activate an item and then travel a specified distance. The cumulative activity statistics for the player may keep a running total of the distance travelled since the item was obtained or activated. As described above, the running total may be a combination of distance travelled obtained from multiple sources, such as virtual distance travelled when the player is actively playing the game and distance imported by the background process for periods when the player is not actively playing the game. If the activity data received from a client device 120 causes the running total to exceed a threshold defined in the game objectives, the notification generation module 540 sends a notification to the client device 120 to notify the player that the objective has been completed.

In another embodiment, other cumulative activity statistics may be used to determine whether a player has completed a game objective. For example, a game objective may require a player to exercise for a certain amount of time within a given time period (e.g., fifteen minutes a day, an hour a week, at least ten minutes a day for five consecutive days, etc.). Thus, the cumulative statistics may include an exercise metric that tracks the amount of time a player spends exercising in each instance of a predetermined time period (e.g., minutes exercise per day) and determine whether the player has completed a game objective based on the exercise metric.

The notification generation module 540 may also generate notifications based on a player's progress towards a game objective. For example, if the imported activity data indicates the player has completed a certain amount (e.g., 50%, 75%, 90% etc.) of the required activity to complete an objective, the notification generation module 540 may generate a corresponding notification to notify the player of their progress and encourage them to undertake physical activity to complete the objective.

The game database 550 includes one or more machine-readable media configured to store game data used in the location-based game to be served or provided to client devices 120 over the network 130. The game data stored in the game database 550 can include: (1) data associated with the virtual world in the location-based game (e.g. imagery data used to render the virtual world on a display device, geographic coordinates of locations in the virtual world, etc.); (2) data associated with players of the location-based game (e.g. player information, player experience level, player currency, player inventory, current player positions in the virtual world/real world, player energy level, player preferences, team information, etc.); (3) data associated with game objectives (e.g. data associated with current game objectives, status of game objectives, past game objectives, future game objectives, desired game objectives, etc.); (4) data associated virtual elements in the virtual world (e.g. positions of virtual elements, types of virtual elements, game objectives associated with virtual elements, corresponding actual world position information for virtual elements, behavior of virtual elements, relevance of virtual elements, etc.); (5) data associated with real world objects, landmarks, positions linked to virtual world elements (e.g. location of real world objects/landmarks, description of real world objects/landmarks, relevance of virtual elements linked to real world objects, etc.); (6) game status (e.g. current number of players, current status of game objectives, player leaderboard, etc.); (7) data associated with player actions/input (e.g. current player positions, past player positions, player moves, player input, player queries, player communications, etc.); and (8) any other data used, related to, or obtained during implementation of the location-based game. The game data stored in the game database 550 can be populated either offline or in real time by system administrators or by data received from players, such as from one or more client devices 120 over the network 130.

The game database 550 may also store real world conditions data. The real-world condition data may include the aggregate locations of players in the real world; player actions associated with locations of cultural value or commercial value; map data providing the locations of roads, highways, and waterways; current and past locations of individual players; hazard data; weather data; event calendar data; activity data for players (e.g., distance travelled, minutes exercised, etc.); and other suitable data. The real-world condition data can be collected or obtained from any suitable source. For example, the game database 550 can be coupled to, include, or be part of a map database storing map information, such as one or more map databases accessed by a mapping service. As another example, the game server 110 can be coupled to one or more external data sources or services that periodically provide population data, hazard data, weather data, event calendar data, or the like.

The activity data store 560 includes one or more machine-readable media configured to store data related to the real-world activity of players. The activity data store 560 may include the raw activity data provided by client devices 120, virtual activity equivalents determined by the activity data ingestion module 530, cumulative statistics determined by the activity data ingestion module 530, or the like, as well as combinations of the preceding data.

Example Method of Importing Activity Data into a Parallel-Reality Game

Figure 6:
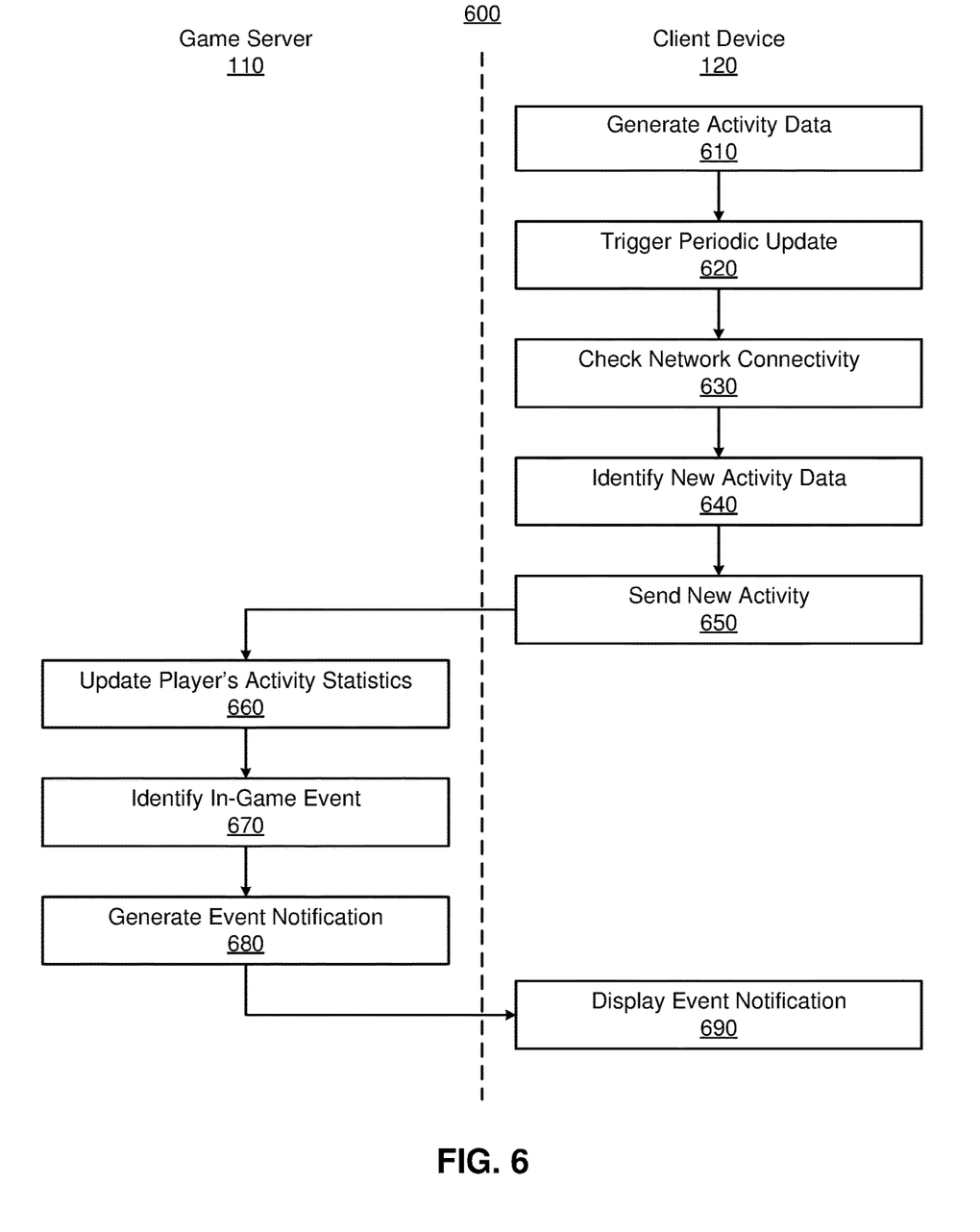
FIG. 6 is an interactions diagram illustrating a method for importing real-world activity data into a location-based game, according to one embodiment.

FIG. 6 is a client-server interaction diagram of an example method 600 for importing activity data into a parallel-reality game, according to one embodiment. The method 600 can be implemented using any suitable client-server architecture, such as the location-based gaming system 100 of FIG. 1. In addition, although FIG. 6 depicts steps performed in a particular order for purposes of illustration and discussion, the methods discussed herein are not limited to any particular order or arrangement. One skilled in the art will appreciate that various steps of the methods disclosed herein can be omitted, rearranged, combined, or adapted in various ways without deviating from the scope of the present disclosure.

In the embodiment shown in FIG. 6, the method 600 begins with the client device 120 generating 610 activity data. As described previously, the activity data may be derived from the output of one or more sensors that are incorporated into the client device 120 or in communication with the client device (e.g., sensors in a wearable device). The activity data may be generated 610 by a fitness application 430, such as the Health app from APPLE® or GOOGLE FIT™.

Either the fitness application 430 or the activity data extraction module 440 may trigger 620 a periodic update. The periodic update causes the client device 120 to check 630 for network connectivity and, assuming the network 130 can be reached, identify 640 new activity data. As described previously, the new activity data may include activity data generated since the previous periodic update. The client device 120 sends 650 the new activity data to the game server 110 via the network 130. If communication of the new activity data to the game server 110 fails, the client device 120 may save the new activity data locally (e.g., in the local data store 460) and add it to the activity data that is generated in the next periodic update. This local accumulation of activity data may be unrestricted (meaning all activity data will ultimately reach the server) or may be subject to time limit, either by the client device 120 deleting or the server rejecting activity data with a time stamp from more than a predetermined time in the past.

The game server 110 may identify the player associated with the activity data based on an identifier of the player (e.g., a username or player ID) or the client device 120 (e.g., a MAC ID or serial number) sent in conjunction with the activity data. In embodiments where an identifier of the client device 120 is used, the game server may store mappings between players and client devices 120 (e.g., in the game database 550) and query the mappings with the received device identifier to identify the corresponding player. Regardless of how the player is identified, the game server 110 updates 660 the cumulative activity statistics for the player (e.g., in the activity data store 560). As described previously, updating 660 the cumulative activity statistics may involve converting some or all of the real-world activity data into corresponding virtual world metrics. For example, steps taken or wheelchair pushes in the real world may be converted into a distance travelled in the virtual world by assuming each step or push is equivalent to traveling a certain distance (e.g., seventy-five centimeters). The distance corresponding to a step or push may be standardized across all players or may be specific to the player (e.g., based on demographic information about the player such as age, gender, and height).

The game server 110 identifies 670 an in-game event based on the updated 660 cumulative activity statistics. As described previously, in-game events may include unlocking a reward once the player has travelled a certain distance (either since starting to play the game or since another in-game event, such as obtaining or activating a particular virtual item). The game server 110 generates 680 an event notification regarding the in-game event and sends it to the client device 120. On receiving the event notification, the client device 120 displays 690 the event notification (e.g., in a notifications bar). Thus, the player may be alerted to the in-game event, which may increase player engagement with the game. Notifications may also notify the player of progress towards an in-game event, encouraging desirable behaviors (e.g., increased exercise to more quickly complete game objectives that are tied to activity requirements).

Example Computing Device Architecture

Figure 7:
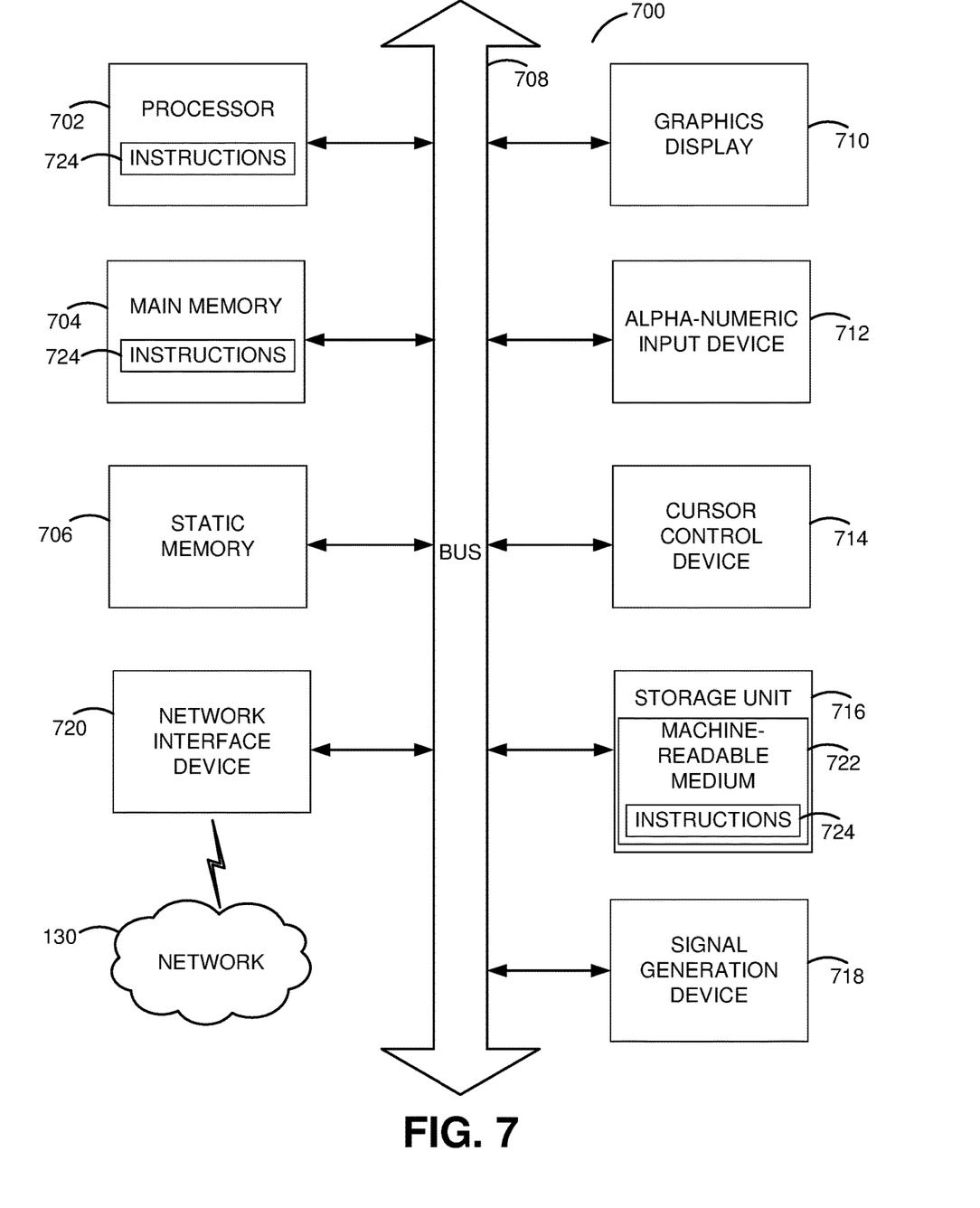
FIG. 7 is a block diagram illustrating an example computer suitable for use in the network computing environment of FIG. 1, according to one embodiment.

FIG. 7 is a block diagram illustrating components of an example machine able to read instructions from a machine-readable medium and execute them in a processor (or controller). Specifically, FIG. 7 shows a diagrammatic representation of a machine in the example form of a computer system 700. The computer system 700 can be used to execute instructions 724 (e.g., program code or software) for causing the machine to perform any one or more of the methodologies (or processes) described herein, including those associated, and described, with the components (or modules) of a game server 110 or client device 120.

The machine may be a server computer, a client computer, a personal computer (PC), a tablet PC, a set-top box (STB), a smartphone, a network router, switch or bridge, a cell phone tower, or any machine capable of executing instructions 724 (sequential or otherwise) that specify actions to be taken by that machine. Further, while only a single machine is shown, the term "machine" shall also be taken to include any collection of machines that individually or jointly execute instructions 724 to perform any of the disclosed methods.

The example computer system 700 includes one or more processing units (generally one or more processors 702). The processor 702 is, for example, a central processing unit (CPU), a graphics processing unit (GPU), a digital signal processor (DSP), a controller, a state machine, one or more application specific integrated circuits (ASICs), one or more radio-frequency integrated circuits (RFICs), or any combination of these. Any reference to a processor 702 may refer to a single processor or multiple processors. The computer system 700 also includes a main memory 704. The computer system may include a storage unit 716. The processor 702, memory 704, and storage unit 716 communicate via a bus 708.

In addition, the computer system 700 can include a static memory 706, a display driver 710 (e.g., to drive a plasma display panel (PDP), a liquid crystal display (LCD), or a projector). The computer system 700 may also include alphanumeric input device 712 (e.g., a keyboard), a cursor control device 714 (e.g., a mouse, a trackball, a joystick, a motion sensor, or other pointing instrument), a signal generation device 718 (e.g., a speaker), and a network interface device 720, which also are configured to communicate via the bus 708.

The storage unit 716 includes a machine-readable medium 722 which may store instructions 724 (e.g., software) for performing any of the methods or functions described herein. The instructions 724 may also reside, completely or partially, within the main memory 704 or within the processor 702 (e.g., within a processor's cache memory) during execution by the computer system 700. The main memory 704 and the processor 702 also constitute machine-readable media. The instructions 724 may be transmitted or received over a network 130 via the network interface device 720.

While the machine-readable medium 722 is shown in an example embodiment to be a single medium, the term "machine-readable medium" should be taken to include a single medium or multiple media (e.g., a centralized or distributed database, or associated caches and servers) able to store the instructions 724. The term "machine-readable medium" shall also be taken to include any medium that is capable of storing instructions 724 for execution by the machine and that cause the machine to perform any one or more of the methods or functions disclosed herein. The term "machine-readable medium" includes, but is not limited to, data repositories in the form of solid-state memories, optical media, and magnetic media.

While the present subject matter has been described in detail with respect to specific exemplary embodiments and methods thereof it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations or additions to the present subject matter as would be readily apparent to one of ordinary skill in the art.

Additional Considerations

Some portions of above description describe the embodiments in terms of algorithmic processes or operations. These algorithmic descriptions and representations are commonly used by those skilled in the computing arts to convey the substance of their work effectively to others skilled in the art. These operations, while described functionally, computationally, or logically, are understood to be implemented by computer programs comprising instructions for execution by a processor or equivalent electrical circuits, microcode, or the like. Furthermore, it has also proven convenient at times, to refer to these arrangements of functional operations as modules, without loss of generality.

Reference to servers, databases, software applications, and other computer-based systems, as well as actions taken and information sent to and from such systems, are provided to illustrate various concepts. One of ordinary skill in the art will recognize that the inherent flexibility of computer-based systems allows for a great variety of possible configurations, combinations, and divisions of tasks and functionality between and among components. For instance, server processes may be implemented using a single server or multiple servers working in combination, databases and applications may be implemented on a single system or distributed across multiple systems, and distributed components may operate sequentially or in parallel.

In situations in which the systems and methods access and analyze personal information about players, such as location information, the players may be provided with an opportunity to control whether programs or features collect the information. No such information or data is collected or used until the player has been provided meaningful notice of what information is to be collected and how the information is used. The information is not collected or used unless the player provides consent, which can be revoked or modified by the player at any time. Thus, the player can have control over how information about the player is collected and used by the application or system. In addition, certain information or data can be treated in one or more ways before it is stored or used, so that it is anonymized. For example, a player's identity may be treated so that no personally identifiable information can be determined for the player.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Similarly, use of "a" or "an" preceding an element or component is done merely for convenience. This description should be understood to mean that one or more of the element or component is present unless it is obvious that it is meant otherwise.

Where values are described as "approximate" or "substantially" (or their derivatives), such values should be construed as accurate +/−10% unless another meaning is apparent from the context. From example, "approximately ten" should be understood to mean "in a range from nine to eleven."

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Upon reading this disclosure, those of skill in the art will appreciate still additional alternative structural and functional designs for a system and a process for using ad hoc neural networks to process transactions. Thus, while particular embodiments and applications have been illustrated and described, it is to be understood that the described subject matter is not limited to the precise construction and components disclosed. The scope of protection should be limited only by the following claims.

What is claimed is:

1. A non-transitory computer-readable medium storing executable computer code that, when executed by a computing device, causes the computing device to perform operations comprising:

identifying, via a background process of a client device, that updated activity data describing real-world actions performed by a user of the client device is available from an activity monitoring application of the client device, the updated activity data derived from a sensor of the client device;

sending, via a network, a set of activity data of the updated activity data to a server that hosts an interactive application, the set of activity data usable for completing an objective in the interactive application hosted by the server; and receiving, from the server, a notification of a virtual event within the interactive application, wherein the virtual event was triggered responsive to the set of activity data achieving the objective.

2. The non-transitory computer-readable medium of claim 1, wherein the background process is a player event session triggered by a user activity, and wherein identifying that the updated activity data is available via the background process comprises:

querying, by the player event session, the activity monitoring application for activity data usable to achieve the objective; and identifying the updated activity data based on the querying.

3. The non-transitory computer-readable medium of claim 2, further comprising:

monitoring, by the player event session, a geographic position of the client device using an additional sensor of the client device;

determining additional activity data based on the monitored geographic position; and determining the set of activity data by comparing the updated activity data from the activity monitoring application to the additional activity data, the comparing including deduplicating activity data included in both the updated activity data and the additional activity data.

4. The non-transitory computer-readable medium of claim 2, further comprising:

responsive to the notification of the virtual event, terminating the player event session.

5. The non-transitory computer-readable medium of claim 2, wherein the user activity corresponds to one of a type of real-world action performed by the user or a type of virtual action performed by the user in the interactive application.

6. The non-transitory computer-readable medium of claim 2, further comprising:

responsive to additional user activity, executing an additional player event session in parallel with the player event session;

monitoring, by the additional player event session, a geographic position of the client device using an additional sensor of the client device; and responsive to identifying additional updated activity data based on the monitoring by the additional player event session, sending, via the network, an additional set of activity data of the additional updated activity data to the server that hosts the interactive application, the additional set of activity data usable for completing an additional objective in the interactive application.

7. The non-transitory computer-readable medium of claim 1, wherein the updated activity data includes one or more metrics derived from the sensor of the client device, and wherein sending the set of activity data comprises:

extracting the set of activity data from the updated activity data, the extracting including filtering the updated activity data to include a subset of the one or more metrics usable for completing the objective in the interactive application; and sending the subset of the one or more metrics to the server.

8. The non-transitory computer-readable medium of claim 1, wherein the notification was generated by a process including:

converting the set of activity data into virtual world activity;

updating cumulative activity statistics for a player associated with the client device based on the virtual world activity; and generating the notification responsive to the cumulative activity statistics meeting one or more activity criteria.

9. The non-transitory computer-readable medium of claim 8, wherein the cumulative activity statistics include a distance travelled and the one or more activity criteria include having travelled a predetermined distance since a specified time.

10. The non-transitory computer-readable medium of claim 1, wherein identifying that updated activity data is available comprises receiving a notification from the activity monitoring application that updated activity data is available.

11. The non-transitory computer-readable medium of claim 1, wherein the interactive application is a location-based parallel reality game.

12. The non-transitory computer-readable medium of claim 1, wherein the activity monitoring application is a fitness application.

13. The non-transitory computer-readable medium of claim 1, wherein the updated activity data includes a number of steps or wheelchair pushes the user associated with the computing device has taken since a previous update.

14. A computer-implemented method for importing real-world activity data into an interactive application, the method comprising:

receiving, from a client device, activity data describing real-world actions performed by a user of the client device, wherein the activity data was retrieved from an activity monitoring application by a background process and was derived from a sensor of the client device;

determining the user has completed an objective using the activity data; and initiating a virtual event in the interactive application corresponding to completion of the objective.

15. The method of claim 14, wherein the background process is a player event session of a plurality of player event sessions of the client device, the player event session triggered by a user activity associated with the objective, and further comprising:

receiving, from the client device, context information indicating that the player event session is active on the client device, the context information including a first session identifier for the player event session;

after storing the first session identifier, receiving, from the client device, a second session identifier with the activity data; and responsive to determining that the first session identifier and the second session identifier match, processing the activity data to determine whether the user has completed the objective.

16. The method of claim 14, further comprising:

sending, to the client device, a notification responsive to initiating the virtual event, the notification including instructions that cause the client device to display an indication of the virtual event.

17. The method of claim 14, wherein determining the user has completed the objective comprises:
   converting one or more metrics included in the activity data into virtual world activity;
   updating cumulative activity statistics based on the virtual world activity; and
   determining the user has completed the objective using the updated cumulative activity statistics.

18. The method of claim 17, wherein the activity data includes a number of steps or wheelchair pushes, the virtual world activity includes a distance travelled in a virtual world that corresponds to the number of steps or wheelchair pushes, and the cumulative activity statistics includes a cumulative distance travelled in the virtual world since a specified time.

19. The method of claim 14, wherein the interactive application is a parallel reality game, the objective is a game objective in the parallel reality game, and the virtual event is completion of the game objective.

* * * * *